| United States Patent [19] | [11] Patent Number: 4,730,082 |
| Amiet | [45] Date of Patent: Mar. 8, 1988 |

[54] PROCESS FOR THE PREPARATION OF METHYLTRIFLUOROACETATE

[75] Inventor: Louis Amiet, Lyons, France

[73] Assignee: Rhone-Poulenc Specialties Chimiques, France

[21] Appl. No.: 873,510

[22] Filed: Jun. 12, 1986

[30] Foreign Application Priority Data

Jun. 14, 1985 [FR] France ................................ 85 09024

[51] Int. Cl.$^4$ .......................... C07C 69/63; B01D 3/34
[52] U.S. Cl. ...................................... 560/227; 203/61; 203/66; 203/82; 203/DIG. 6
[58] Field of Search .................... 560/227; 203/66, 82, 203/61, DIG. 6

[56] References Cited

U.S. PATENT DOCUMENTS 2,649,407  8/1953  Harrison et al. ................... 203/66 X
4,250,328  2/1981  Fujita et al. .............. 203/DIG. 6 X
4,435,595  3/1984  Agreda et al. ............ 203/DIG. 6 X

OTHER PUBLICATIONS

Hagen, Miller, et al., 47, J. of Organic Chemistry, 1345–47, (1982).
Moffat & Hunt, 79, J. of the American Chemical Society, 54, (1957).
Moffat & Hunt, 81, J. of the American Chemical Society, 2082–86, (1959).

Primary Examiner—Donald B. Moyer
Assistant Examiner—Patricia M. Scott
Attorney, Agent, or Firm—Finnegan, Henderson, Farabow, Garrett & Dunner

[57] ABSTRACT

A process for the preparation of methyltrifluoroacetate. Trifluoroacetic acid is contacted with an excess of methanol and distilled to form a methyltrifluoroacetate/methanol azeotrope. The azeotrope is contacted with trifluoroacetic acid in the presence of a catalytic quantity of a strong acid followed by distillation to obtain methyltrifluoroacetate. The methyltrifluoroacetate can be used as a synthesis intermediate in the pharmaceutical industry.

14 Claims, 1 Drawing Figure

PROCESS FOR THE PREPARATION OF METHYLTRIFLUOROACETATE

BACKGROUND OF THE INVENTION

The present invention relates to a process for the preparation of methyltrifluoroacetate. Since methyltrifluoroacetate is used as a synthesis intermediate in the pharmaceutical industry, a high purity is often required. The present invention makes it possible to meet this objective.

Previously, as described in Hagen, Miller, Bynum, Kapila 47 *Journal of Organic Chemistry* 1345-1347 (1982), methyltrifluoroacetate has been prepared by the condensation of trifluoroacetic acid with methanol followed by a simple distillation. The process achieves an ester yield of 100% having a boiling point of 49°-51° C. However, in view of the fact that the boiling point of the pure methyl ester of trifluoroacetic acid is 41°-43° C. (Beilstein E IV-2 p. 463), the product obtained by the process in this article cannot consist of pure methyltrifluoroacetate.

The art also discloses the preparation of trifluoroacetic acid esters by reacting an alcohol with an excess of trifluoroacetic acid in the presence of a catalyst of sulfuric acid. The ester is then washed with water. Moffat and Hunt, 79 *Journal of the American Chemical Society* 54 (1957) and 81 *Journal of the American Chemical Society* 2082-86 (1959). During the washing of the ester with water, a partial hydrolysis takes place and, hence, the excess trifluoroacetic acid and the products of hydrolysis are highly diluted in the aqueous medium. As a result, they can only be recovered for industrial use with great difficulty. These two drawbacks render this process industrially unexploitable, especially from an economic point of view, because the starting raw materials, especially trifluoroacetic acid, are very expensive.

Research Disclosure No. 299,359 discloses the condensation of trifluoroacetic acid with an aliphatic alcohol containing a short alkyl chain in the presence of a catalytic quantity of a strong mineral acid. The organic phase is then treated with a strong mineral acid and, finally, distilled to obtain the ester. In this process, the trifluoroacetic acid and the alcohol are used in approximately equimolar quantities.

When a small excess, such as 5%, of methanol relative to the quantity of trifluoroacetic acid is used in the preparation of methyltrifluoroacetate, in the presence of large quantities of sulfuric acid, the yield of the esterification reaction is not quantitative. When catalytic quantities of sulfuric acid are employed, water is distilled with the ester. This gives rise to a slight hydrolysis with the formation of trifluoroacetic acid that cannot be recovered. If a larger excess of methanol is used, pure methyltrifluoroacetate cannot be separated, because of the existence of an azeotrope of methyltrifluoroacetate and methanol. If an excess of trifluoroacetic acid relative to methanol is used, either the excess added is lost, which is not very useful from an economic point of view in view of the price of trifluoroacetic acid, or a very complicated recovery process must be developed because trifluoroacetic acid forms an azeotrope with water.

Thus, none of these previous processes makes it possible to manufacture methyltrifluoroacetate in an industrially viable manner.

SUMMARY OF THE INVENTION

The present invention has made it possible to solve these problems by providing a simple, effective, economical, and readily usable process for the preparation of methyltrifluoroacetate. The process contacts trifluoroacetatic acid with an excess of methanol and then distills the trifluoroacetic acid and methanol to form a methyltrifluoroacetate/methanol azeotrope. The azeotrope is brought into contact with trifluoroacetic acid in the presence of a catalytic quantity of a strong acid. The reaction mixture is then distilled to obtain methyltrifluoroacetate.

The process of the present invention is a discontinuous process that makes it possible to esterify all of the trifluoroacetic acid introduced into the reaction. As a result, pure methyltrifluoroacetate is obtained without the need of subjecting the trifluoroacetic acid/water mixture to a difficult separation procedure.

The above and other features and advantages of the present invention will be made more apparent from the following description of the preferred embodiment.

DESCRIPTION OF THE DRAWING

The accompanying FIG. 1, which is incorporated in and constitutes a part of the specification, illustrates an embodiment of the invention and, together with the description, serves to explain the principles of the invention.

DETAILED DESCRIPTION OF THE PREFERRED EMBODIMENT

Figure 1:
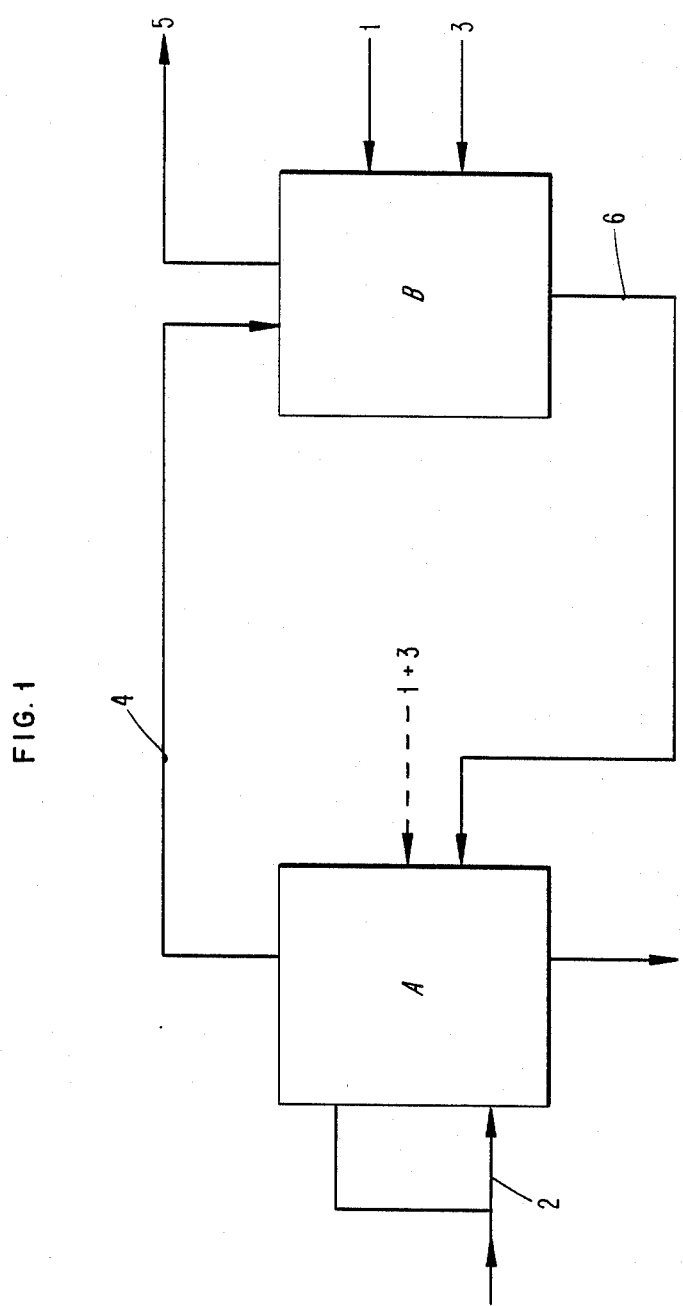
FIG. 1 is a schematic drawing illustrating one embodiment of the process of the present invention.

The present invention provides a process for the preparation of methyltrifluoroacetate. In the first step of the process, trifluoroacetic acid is contacted with an excess of methanol. In one embodiment of the present invention, as shown in FIG. 1, trifluoroacetic acid (1) and methanol (2) are introduced into a reactor chamber A using a molar ratio of methanol to trifluoroacetic acid of at least 2.30. A catalytic quantity of a strong acid (3), chosen especially from sulfuric acid and phosphoric acid, can be added either with or without a carrier into chamber A.

In the second step of the process, the trifluoroacetic acid and methanol are distilled to form a methyltrifluoroacetate/methanol azeotrope. In one embodiment, the reactor chamber A is heated to distill a methyltrifluoroacetate/methanol azeotrope (4) having a boiling point of 37° C.-38° C. at a pressure of 98,000 pascals. In the azeotrope, the methanol content is approximately 6% by weight. The heating of the reactor chamber A is also continued to distill the methanol (1) that will then be recycled to be used in the first step of the process. The residue in the reactor chamber A contains mineral acid and water of esterification, and it is discarded.

In the third step of the process, the methyltrifluoroacetate/methanol azeotrope is brought into contact with trifluoroacetic acid in the presence of a catalytic quantity of a strong acid to form a mixture. This mixture is then distilled to obtain methyltrifluoroacetate. In one embodiment of the present process, the methyltrifluoroacetate/methanol azeotrope (4) is introduced from reactor chamber A into reactor chamber B with an excess of trifluoroacetic acid (1) relative to the methanol contained in the azeotrope. A catalytic quantity of a strong acid (3), such as a mineral acid, is also introduced into the reactor chamber B. The same strong acid used in reactor chamber A can also be used in reactor chamber B. Methyltrifluoroacetate (5) is then distilled from the reaction mixture. The methyltrifluoroacetate has a boiling point between 41° C. and 42° C. at a pressure of 98,000 to 101,000 pascals.

The resulting residue (6) formed in chamber B contains the excess trifluoroacetic acid, the water generated by the esterification of the methanol contained in the methyltrifluoroacetate/methanol azeotrope, and the strong mineral acid (3) used as catalyst. This residue (6) can be recycled to chamber A for use in place of the addition of pure trifluoroacetic acid and the strong acid catalyst.

Therefore, this process makes it possible to introduce trifluoroacetic acid alone in reactor chamber B and an excess of methanol alone in reactor A, which is recycled, and use a catalytic quantity of strong acid. The only losses are the catalyst and the water formed during esterification.

Reactor chambers A and B may be a single reactor or two different reactors. The two contacting and distillation stages can be carried out either sequentially or simultaneously.

The strong acids are preferably mineral acids chosen from sulfuric acid and phosphoric acid. The strong acids can be used with or without carriers.

According to a preferred embodiment of the invention, the molar ratio of the methanol introduced into reactor A to trifluoroacetic acid (1) introduced into reactor B is at least about 2.30 and, preferably, at least about 2.35. In fact, below this limit, the methyltrifluoroacetate/methanol azeotrope entrains some water. The weight ratio of the strong mineral acid to trifluoroacetic acid brought brought into contact with the methyltrifluroacetate/methanol azeotrope is preferably from about 0.25 to 1% and, even more preferably, from about 0.3 to 0.5%.

The methyltrifluoroacetate made in the present process can be used as a synthesis intermediate in the manufacture of compounds for plant protection or pharmaceutical activity. For such syntheses, see French Pat. No. 2,416,883.

The following are illustrated examples of the present invention. It is understood, however, that the invention is not to be limited to the specific conditions or details set forth in these examples, except insofar as such limitations are specified in the claims.

EXAMPLE 1 INITIATION OF THE PREPARATION CYCLE

A 6-liter round glass flask is equipped with a stirring system, a thermometer, and a dropping funnel. The flask is connected to a 30-plate Oldershaw glass distillation column with the usual condensation and recovery system. It is loaded sequentially with 2,201 g (19.3 moles) of pure trifluoroacetic acid (TFA) followed by 1,448 g of pure methanol (CH$_3$OH) over 0.5 hour with slight stirring. Finally, 13 g of pure concentrated (98%) H$_2$SO$_4$ are added. The mixture is heated to reflux temperature at ambient atmospheric pressure and the temperature of the column heat stabilizes between 37.5° C. and 38° C. At a reflux ratio of 3 to 4, 2,560 g of a fraction A made up of a mixture containing, according to analysis, 91.7% of methyltrifluoroacetic acid (MTFA), 1.3% of TFA, and 7% of CH$_3$OH are collected. A fraction B that distills at 63° C. consists of CH$_3$OH and weighes 674.5 g. 20 g of an intermediate fraction C is distilled at 65° C. to 95° C. A residue of 320 g is discarded.

2nd stage of the cycle

In the same apparatus as before, 2,064 g of the fraction A are placed, 2,271 g of TFA and 13 g of H$_2$SO$_4$ are added, and the mixture is heated to reflux. The temperature gradually stabilizes at 41°–41.5° C. At a reflux ratio of 5, a 2,430 g mass, analyzed by NMR as containing 99.7% of pure MTFA, is recovered. The distillation is stopped as soon as the temperature approaches 41.6° C.–41.8° C. and the residue R is stored.

1st Stage of the Recycle 1,490 g of CH$_3$OH are added to the entire residue R and the mixture is heated to reflux. As in the case of the initiation stage described above, a fraction weighing 2,087 g is distilled at 37.5°–38° C. and contains 92% of MTFA, 7% of CH$_3$OH and approximately 1% of TFA. The excess methanol (830 g) and an intermediate weighing 18 g are separated sequentially. A residue weighing 338 g is discarded. The analysis of the residue does not make it possible to detect any F$^-$ ion within the sensitivity limit of the method, which is 5 mg/l. A total F content of 260 mg/l was measured. This total F content corresponds to traces of trifluoroacetic acid and esters.

EXAMPLE 2

The same apparatus as in Example 1 is used and the same procedure is followed, employing, in the course of the initiation cycle:

2,188 g (19.2 moles) of trifluoroacetic acid;
2,000 g (62.5 moles) of methanol; and 7 g of sulfuric acid.

At 37° C. at the column head, a distillate that corresponds to the azeotrope is produced. methyl trifluoroacetate (MTFA)/methanol weighing 2,626 g followed by 1,188 g of methanol and a 22 g of an intermediate fraction distilling at 63° C. to 97° C. are collected. A residue of 320 g is discarded.

In the course of the second stage, according to the process, the following are used:

2,615 g of an azeotrope containing MFTA/methanol;
2,850 g of trifluoroacetic acid; and
13.8 g of sulfuric acid.

A distillate containing 3,045 g of methyltrifluoroacetate with a MTFA purity of 99.7% is collected. A residue R remains.

In the course of the recycle of the first step according to the process of the invention, the following are introduced into the reactor containing the residue R:

1,188 g of methanol from the distillate of the previous initiation stage; and
812 g of additional methanol. This produces a distillate of:
2,815 g of a MTFA/methanol azeotrope;
1,135 g of methanol; and
20 g of an intermediate fraction.
435 g of residue are discarded.
In the course of the second stage of this new cycle:
2,790 g of the MTFA/methanol azeotrope;
2,850 g of trifluoroacetic acid; and
10.5 g of concentrated sulfuric acid (98%) are introduced.

A distillate weighing 3,085 g of methyltrifluoroacetate and a residue weighing 2,482 g, which is recycled, if appropriate, towards a third cycle of preparation, are collected.

EXAMPLE 3

Into a 0.5-liter round flask equiped with the same system as in Example 1 and with a 10-plate distillation column, 160 g of methanol (5 moles) are introduced. Then, over a period of 30 minutes, the following are introduced with gentle stirring:

175 g of trifluoroacetic acid (1.53 mole); and
1.4 g of 85% phosphoric acid.

The mixture is heated to reflux and the temperature at the column head stabilizes at 38° C. 195 g of the methyltrifluoroacetate/methanol azeotrope are distilled.

In the course of the 2nd stage:
100 g of the MTFA/methanol azeotrope obtained previously;
114 g of trifluoroacetic acid; and
1 g of phosphoric acid are introduced.

This mixture is then heated to reflux and, at a temperature of between 41° C. and 41.5° C. at the column head, a 112 g fraction of methyltrifluoroacetate is distilled.

What is claimed is:

1. A process for the preparation of methyltrifluoroacetate comprising the steps of:
   (a) containing trifluoroacetic acid with an excess of methanol;
   (b) distilling the trifluoroacetic acid and methanol to form a methyltrifluoroacetate/methanol azeotrope;
   (c) contacting the azeotrope with trifluoroacetic acid in the presence of a catalytic quantity of a strong acid to form a mixture; and
   (d) distilling the mixture to obtain methyltrifluoroacetate and a residue.

2. The process according to claim 1, further comprising the step of continuing the distillation of step (b) to distill excess methanol.

3. The process according to claim 2, wherein the distilled methanol is recycled for use in step (a).

4. The process according to claim 1, wherein the residue from step (d) contains trifluoroacetic acid and is recycled for use in step (a).

5. The process according to claim 1, wherein the molar ratio of methanol used in step (a) to trifluoroacetic acid used in step (c) is greater than or equal to about 2.30.

6. The process according to claim 5, wherein the molar ratio is greater than or equal to about 2.35.

7. The process according to claim 1, wherein the weight ratio of strong acid to trifluoroacetic acid used in step (c) is from about 0.25 to 1%.

8. The process according to claim 7, wherein the weight ratio is from about 0.3 to 0.5%.

9. The process according to claim 1, wherein the strong acid is selected from the group consisting of sulfuric acid and phosphoric acid.

10. The process according to claim 1, wherein the step (a) the contacting of the trifluoroacetic acid is conducted in the presence of a catalytic quantity of a strong acid.

11. The process according to claim 10, wherein the strong acid is selected from the group consisting of sulfuric acid and phosphoric acid.

12. The process according to claim 10, wherein the weight ratio of strong acid trifluoroacetic acid used in step (a) is from about 0.25 to 1%.

13. The process according to claim 1, wherein (1) steps (a) and (b) and (2) steps (c) and (d) are carried out sequentially.

14. The process according to claim 1, wherein steps (a) and (c) are carried out simultaneously and steps (b) and (d) are carried out simultaneously.

* * * * *